US010610655B2

(12) United States Patent
Bailey et al.

(10) Patent No.: US 10,610,655 B2
(45) Date of Patent: Apr. 7, 2020

(54) INTUBATION WITH AUDIOVIBRATORY GUIDANCE

(71) Applicant: OHIO STATE INNOVATION FOUNDATION, Columbus, OH (US)

(72) Inventors: Robert Bailey, West Jefferson, OH (US); Hamdy Mohamed Elsayed-Awad, Upper Arlington, OH (US); Joseph Dean West, Richwood, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 456 days.

(21) Appl. No.: 15/518,172

(22) PCT Filed: Oct. 20, 2015

(86) PCT No.: PCT/US2015/056453
§ 371 (c)(1),
(2) Date: Apr. 10, 2017

(87) PCT Pub. No.: WO2016/064870
PCT Pub. Date: Apr. 28, 2016

(65) Prior Publication Data
US 2017/0304571 A1    Oct. 26, 2017

Related U.S. Application Data

(60) Provisional application No. 62/066,020, filed on Oct. 20, 2014.

(51) Int. Cl.
*A61B 1/267* (2006.01)
*A61B 7/02* (2006.01)
(Continued)

(52) U.S. Cl.
CPC ..... *A61M 16/0488* (2013.01); *A61B 1/00006* (2013.01); *A61B 1/0008* (2013.01);
(Continued)

(58) Field of Classification Search
CPC . A61B 1/00006; A61B 1/0008; A61B 1/0016; A61B 1/276; A61B 1/00133;
(Continued)

(56) References Cited

U.S. PATENT DOCUMENTS 4,445,501 A * 5/1984 Bresler ............... A61B 5/06
128/207.14
5,331,967 A * 7/1994 Akerson ............. A61M 16/04
128/207.14
(Continued)

FOREIGN PATENT DOCUMENTS

WO    2010/114920    10/2010

OTHER PUBLICATIONS

Awad et al., "Robotic Surgeries in Patients with Advanced Glaucoma," Anesthesiology, 2013—vol. 119—Issue 4—p. 954.
(Continued)

*Primary Examiner* — John P Leubecker
(74) *Attorney, Agent, or Firm* — Michael Best & Friedrich LLP

(57) ABSTRACT

Systems and methods are provided for inserting an endoscope through an anatomical cavity to a target site. A speaker is positioned externally proximate to a patient and the endoscope is inserted into the anatomical cavity. A signal is received from at least one sensor positioned near the distal end of the endoscope. The signal is indicative of vibrations induced in internal cavity tissue by the externally positioned speaker. A first anatomical structure in contact with the distal end of the endoscope is identified based on the signal indicative of vibrations induced in the internal cavity tissue (Continued)

by the externally positioned speaker. As the distal end of the endoscope moves from the first anatomical structure into contact with other anatomical structures along a path to the target site, the received signal indicative of induced vibrations changes correspondingly and is used to guide the endoscope to the target site.

13 Claims, 11 Drawing Sheets

(51) Int. Cl.
    *A61B 5/06* (2006.01)
    *A61M 16/04* (2006.01)
    *A61B 1/00* (2006.01)
    *A61B 5/00* (2006.01)
    *A61M 16/06* (2006.01)

(52) U.S. Cl.
    CPC ........ *A61B 1/0016* (2013.01); *A61B 1/00055* (2013.01); *A61B 1/00154* (2013.01); *A61B 1/267* (2013.01); *A61B 5/062* (2013.01); *A61B 5/067* (2013.01); *A61B 5/6885* (2013.01); *A61B 5/7405* (2013.01); *A61B 7/023* (2013.01); *A61M 16/06* (2013.01); *A61M 2205/332* (2013.01); *A61M 2205/3317* (2013.01); *A61M 2205/3375* (2013.01); *A61M 2205/50* (2013.01); *A61M 2205/581* (2013.01); *A61M 2205/582* (2013.01)

(58) Field of Classification Search
    CPC ......... A61B 5/061; A61B 5/062; A61B 5/067; A61B 5/6885; A61B 8/0833; A61B 8/4205; A61M 2205/3375
    See application file for complete search history.

(56) References Cited

U.S. PATENT DOCUMENTS

| | | | | |
|---|---|---|---|---|
| 5,445,144 | A * | 8/1995 | Wodicka | A61M 25/0105 128/207.14 |
| 5,560,351 | A * | 10/1996 | Gravenstein | A61M 16/0488 128/200.26 |
| 5,785,051 | A * | 7/1998 | Lipscher | A61B 5/06 128/200.26 |
| 5,823,965 | A * | 10/1998 | Rasmussen | A61B 5/085 600/462 |
| 5,951,461 | A * | 9/1999 | Nyo | A61B 1/00149 600/102 |
| 6,164,277 | A | 12/2000 | Merideth | |
| 6,705,319 | B1 * | 3/2004 | Wodicka | A61M 16/0488 128/200.26 |
| 8,000,771 | B2 * | 8/2011 | Haldeman | A61B 5/02 600/424 |
| 8,522,787 | B2 * | 9/2013 | Lin | A61B 8/0833 128/207.15 |
| 8,594,799 | B2 | 11/2013 | Haller et al. | |
| 8,753,292 | B2 * | 6/2014 | Ingold, Jr. | A61B 5/061 600/586 |
| 10,206,607 | B2 * | 2/2019 | Prough | A61B 5/0095 |
| 2002/0074002 | A1 * | 6/2002 | Tung | A61M 16/04 128/207.14 |
| 2002/0173799 | A1 * | 11/2002 | Besharim | A61M 16/0488 606/108 |
| 2003/0034035 | A1 | 2/2003 | Raphael | |
| 2005/0279355 | A1 | 12/2005 | Loubser | |
| 2006/0081255 | A1 | 4/2006 | Miller et al. | |
| 2008/0269646 | A1 * | 10/2008 | Chau | A61B 5/11 600/595 |
| 2009/0044799 | A1 * | 2/2009 | Qiu | A61B 5/0836 128/200.26 |
| 2012/0089014 | A1 | 4/2012 | Sabczynski et al. | |

OTHER PUBLICATIONS

Awad et al., "The future of robotic cardiac surgery," Journal of Cardiothoracic and Vascular Anesthesia, 2002, vol. 16, Issue 4 , pp. 395-396.
Hemmerling et al., "First robotic tracheal intubations in humans using the Kepler intubation system," BR J Anaesth., 2012, 108(6)1011-6.
Hemmerling et al., "The Kepler Incubation System," Anesthesia & Analgesia, 2012, vol. 114, Issue 3, p. 590-594.
International Search Report and Written Opinion for Application No. PCT/US2015/056453 dated Jan. 5, 2016 (15 pages).
Intuitive Surgical, Inc., "High Level LOE Robotic Publications 2008—4Q 2013," 2014, 47 pages.
Ng et al., "Current status of robot-assisted surgery," Hong Kong Med J., 2014, 20(3)241-50.
Tighe et al., "Robot-assisted airway support: a simulated case," Anesth Analg, 2010, 111(4):929-31.

* cited by examiner

INTUBATION WITH AUDIOVIBRATORY GUIDANCE

CROSS-REFERENCE TO RELATED APPLICATION(S)

This is a U.S. national stage entry of International Patent Application No. PCT/US2015/056453, filed on Oct. 20, 2015, which claims priority to U.S. Provisional Patent Application No. 62/066,020, filed on Oct. 20, 2014, the entire contents of all of which are fully incorporated herein by reference.

BACKGROUND

The present invention relates to systems and methods for placement of a flexible breathing tube into the trachea to maintain an open airway and/or to serve as a conduit through with to administer certain medical therapies (e.g., drugs)—also known as tracheal intubation.

SUMMARY

With nearly 25 million intubations performed each year in the U.S., and roughly 2% ending in failure, there is a need, with that many lives at stake, for improved technology. Various systems and methods described herein provide robotic-based solutions that intubate persons with greater accuracy than is humanly possible and thereby reduces or eliminates the number of failures and other problems in airway management. Furthermore, by being autonomously controlled, the systems can be used by first responders and military personnel for medical emergencies thereby saving additional lives outside the operating room.

In one embodiment, the invention provides an endoscope-type robotic device that is propelled by an electric motor. The motor is controlled by a computer-based controller that receives information about the location of the tip of the endoscope through signals from various sensors—including one or more magnetometers and one or more accelerometers—located near the tip of the endoscope. These sensors generate signals that are responsive to a transponder (i.e., a small loudspeaker) positioned on the subject's neck near the Adam's apple. Vibrations caused by sound waves from the loudspeaker are conducted at varying amplitudes by different anatomical structures. These vibrations are detected by the accelerometer and monitors by the controller. The magnetometers monitor a magnetic field generated by a magnet of the loudspeaker (or, in some constructions, a separate permanent or electro-magnet). The controller controls the insertion and turning direction of the endoscope based on the monitored vibrations and magnetic field. Once the tip of the endoscope has passed through the vocal folds (i.e., the vocal chords) and into the larynx, the endoscope becomes a mechanical guide for an endotracheal tube that is inserted around the endoscope to complete intubation.

In some embodiments, the invention provides a method of robotically guided intubation. A loudspeaker is positioned proximal to the neck of a subject and activated to generate audio vibration of the anatomic structures. A controller causes a motor to advance a controlled endoscope into the airway of the subject. The controller receives a signal from an accelerometer positioned at a distal end of the endoscope and compares the signal to a threshold. When the signal exceeds a first threshold, the controller determines that the distal end of the endoscope is in contact with the epiglottis of the subject and controllably turns the distal end of the endoscope downward. When the signal subsequently exceeds a second, higher threshold, then the controller determines that the distal end of the endoscope is in contact with the laryngeal inlet. The controller then stops insertion of the endoscope.

In some such embodiments, a flexible tube is then extended around the endoscope and inserted through the trachea to the larynx of the subject. In some embodiments, the loudspeaker includes a magnet that generates a magnetic field. The controller continually monitors a signal from a magnetometer positioned in the distal end of the endoscope to determine whether the endoscope tip is centered and, if not, the controller moves the tip of the endoscope laterally.

In some embodiment, the controller monitors whether the signal from the accelerometer falls below the first threshold after contact with the epiglottis is detected. When the signal from the accelerometer falls below the first threshold, the controller determines that contact between the distal tip of the endoscope and the epiglottis has been lost and controllably turns the distal end of the endoscope downward until contact between the distal tip of the endoscope and the epiglottis is reestablished (i.e., the signal from the accelerometer again exceeds the first threshold).

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Successful intubation on a trauma patient requires the placement of an endotracheal tube within the trachea to facilitate external oxygen delivery. Navigating the endotracheal tube is a skill learned through intensive training and only mastered with experience. When dealing with robotic navigation through biological systems, rapidly changing and unique environments must be accounted for. The systems and methods described below utilize magnetic localizing to place an absolute reference of the tip of an endoscopic robot inserted through the trachea of a patient. Sonic excitation is also used to identify key biological landmarks that will guide the insertion process.

Figure 1:
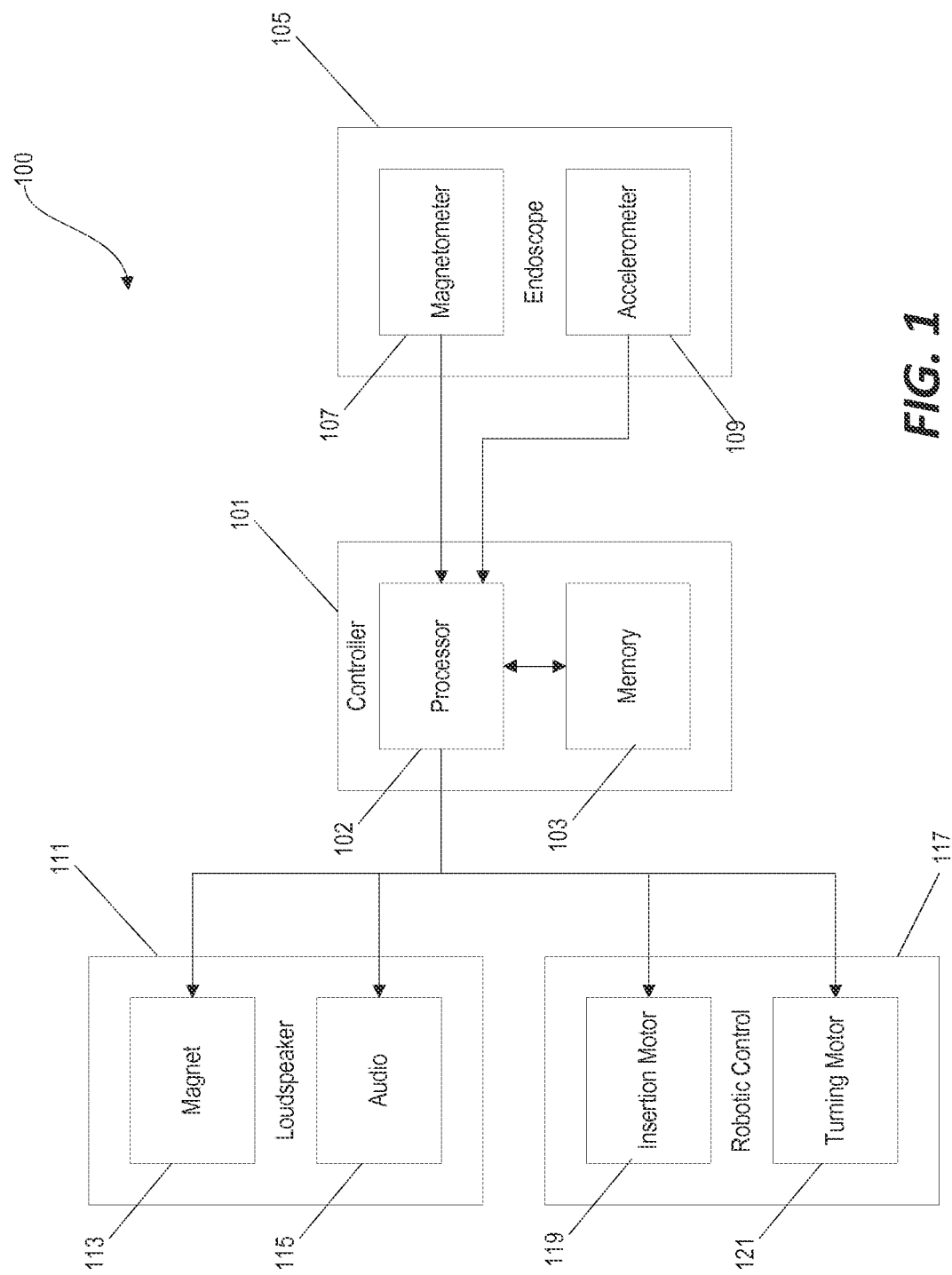
FIG. 1 is a block diagram of an autonomous robotic intubation system according to one embodiment.

FIG. 1 illustrates an example of a system 100 that takes advantage of audio conductivity of various anatomical structures to autonomously guide an endoscopic robot to facilitate the intubation process. A controller 101 includes a processor 102 and memory 103. In this example, the memory 103 is a non-transient, physical computer-readable memory device such as, for example, one or more flash memory modules or a hard drive. In other embodiments, the memory 103 may be replaced with other non-transient, physical computer-readable memory devices such as, for example, RAM or ROM. The memory 103 stores instructions that are executed by the processor 102 to control the operation of the system 100.

The controller 101 receives output signals from a number of sensors positioned at the distal end of an endoscope 105. These sensors include a magnetometer 107 that detects magnetic fields acting on the distal tip of the endoscope and an accelerometer 109 that is configured to detect vibrations. In some constructions, a gyroscopic sensor is positioned at the distal end of the endoscope in addition to or instead of the accelerometer and/or the magnetometer. The controller 101 provides output signals to control the operation of a loudspeaker 111. The loudspeaker in this example includes a magnet 113 and an audio output 115. The controller 101 also provides output signals to provide robotic control 117 of the robotic endoscope. In particular, the controller 101 controls an insertion motor 119 that advances the endoscope into the anatomy and a turning motor 121 that controls lateral movement of the endoscope tip and provides for steering of the endoscope tip.

Figure 2:
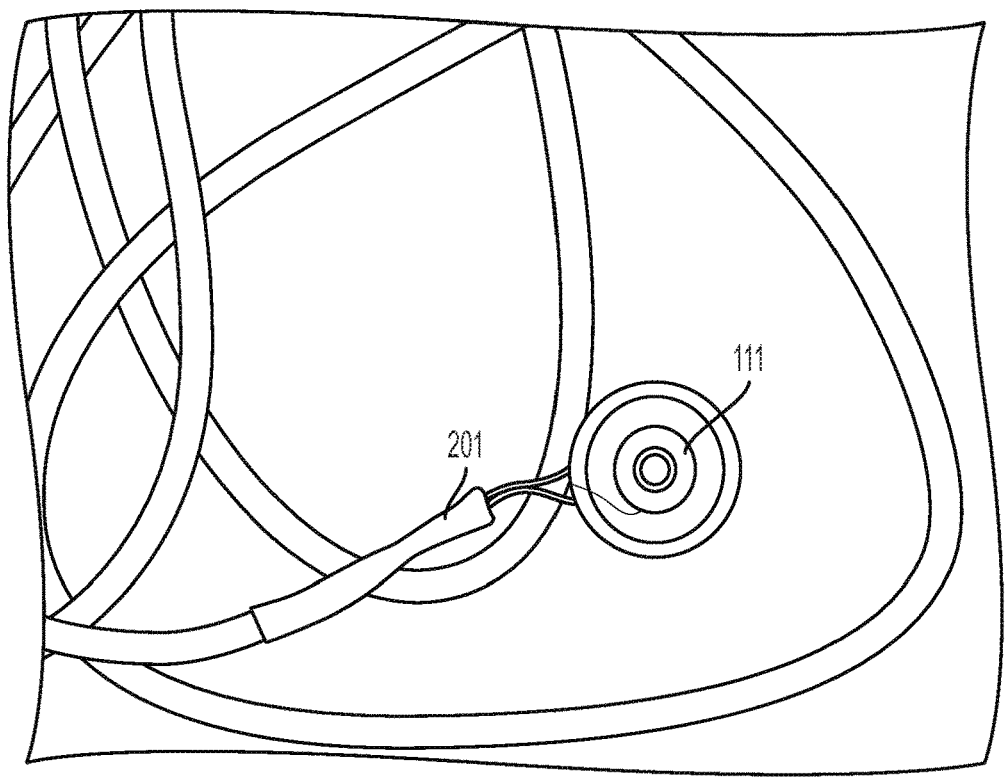
FIG. 2 is a perspective view of an external transducer of the system of FIG. 1.

FIG. 2 illustrates an example of the loudspeaker 111 that acts as a transducer which causes vibration of anatomical structures of the patient. In this example, the loudspeaker 111 is a 100 hz speaker with a 1 inch diameter that is capable of battery-powered operation. However, in other constructions, speakers of other sizes and operating characteristics may be used. As described in detail below, this audiovibratory response allows the controller to detect contact with specific anatomical structures as the endoscope is inserted towards the larynx. In the example of FIG. 2, the loudspeaker 111 is coupled to the controller by an audio cable 201. However, in other implementations, the loudspeaker 111 may or may not require a wired audio cable.

Figure 3:
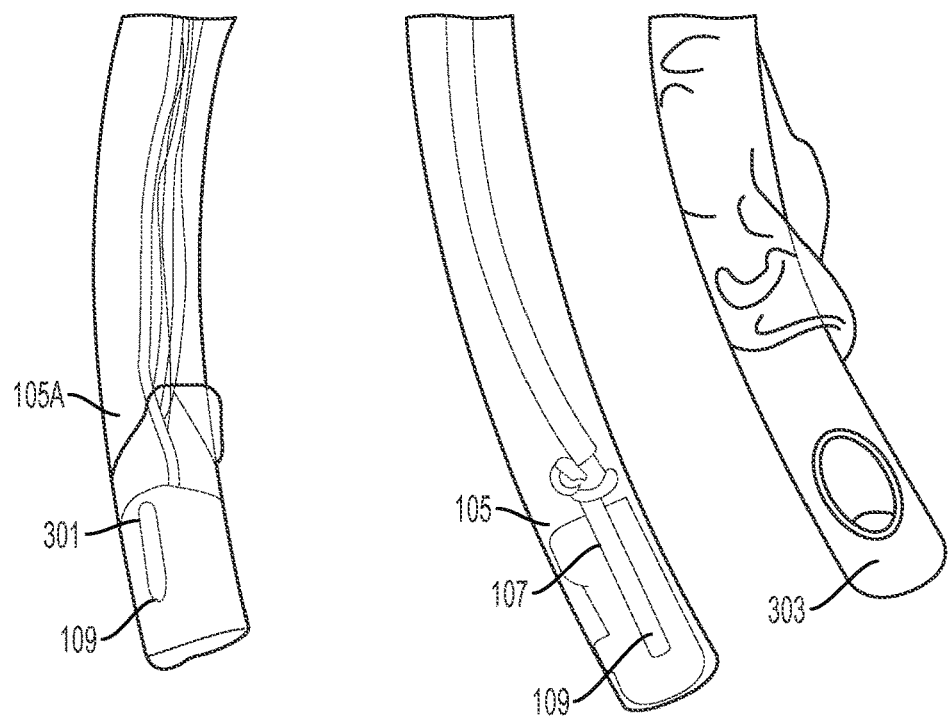
FIG. 3 is a perspective view of two endoscopes of the system of FIG. 1 and an intubation tube.

FIG. 3 illustrates the tip of the endoscope 105 in further detail. As noted above, the endoscope tip is equipped with an accelerometer 109 that produces a signal responsive to vibrations caused by the loudspeaker 111 and a magnetometer 107 that produces a signal indicative of a magnetic field acting upon the distal tip of the endoscope. This endoscope is capable of 6 Degree-of-Freedom (DOF) control using both vibration and magnetic tracking. FIG. 3 also illustrates an alternative construction of the endoscope tip 105 where the tip is equipped with an acceleration sensor 109. However, instead of positioning a magnetometer in the distal tip of the endoscope 105A, a permanent magnet 301 is positioned to generate a magnetic field internally. In such constructions, a magnetic field sensor/magnetometer is placed external to the patient to monitor absolute location of the distal tip of the endoscope 105A. In still other constructions, the system can provide one DOF control by omitting the magnetic sensor and operating based only on vibratory tracking.

FIG. 3 also illustrates a flexible plastic intubation tube 303. As described further below, after insertion of the endoscope is complete, the proximal end of the endoscope can be placed inside of the intubation tube 303 so that the intubation tube 303 can be rapidly inserted to the larynx. The endoscope is then removed leaving only the properly placed intubation tube 303. Alternatively, the intubation tube 303 can be placed around the endoscope before insertion begins such that the intubation tube 303 is inserted along with the endoscope.

Figure 4:
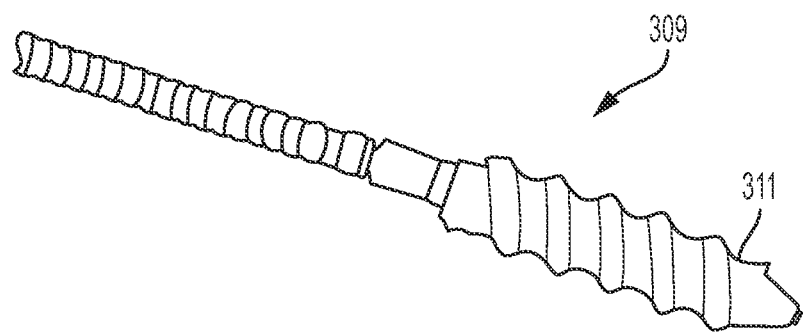
FIG. 4 is a perspective view of an auger-type tip for the endoscope in one embodiment of the system of FIG. 1.

As illustrated in FIG. 4, the distal tip of the endoscope 309 may be equipped with a soft auger 311. The soft material of the auger 311 minimizes trauma that might otherwise occur when the endoscope comes into contact with tissue within the oral cavity and airway. The spiral (e.g., "screw") shape of the auger 311 also helps pull the endoscope forward should it become obstructed or stuck against a fleshy part of the oral cavity and airway. Thus, it is possible to move the endoscope forward with a combined push force (provided by the external actuator (described below)) and pull force (provided by rotation of the auger 311).

Figure 5A:
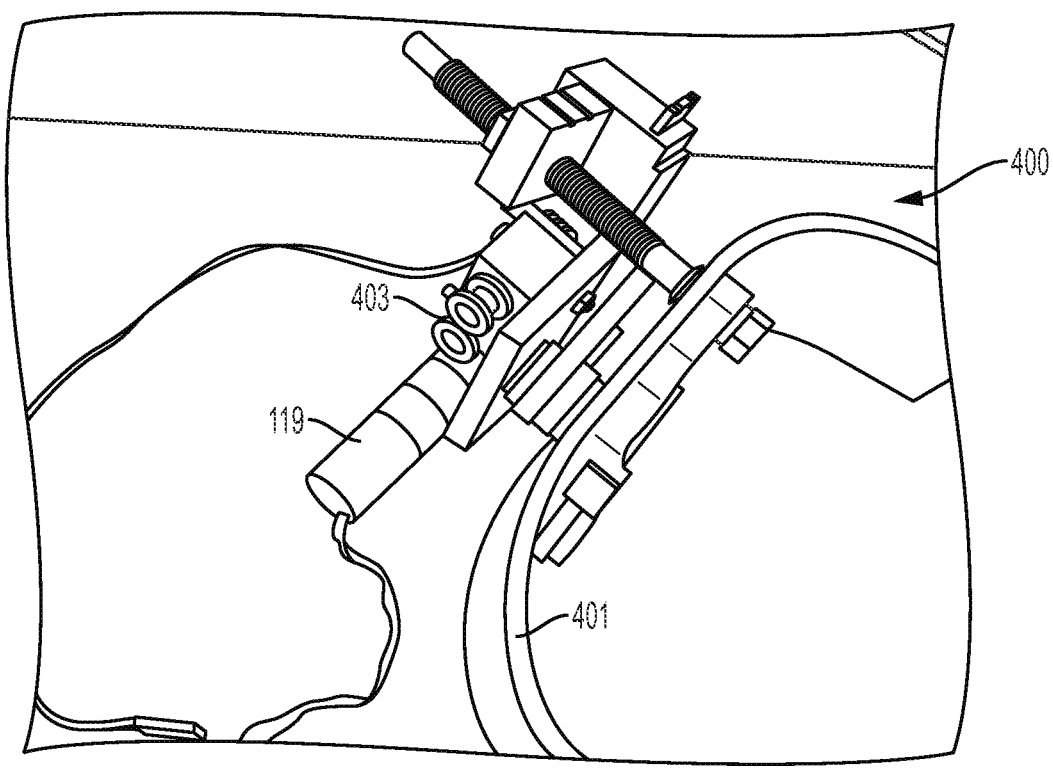
FIG. 5A is a perspective view of an insertion motor mask of the system of FIG. 1.
Figure 5B:
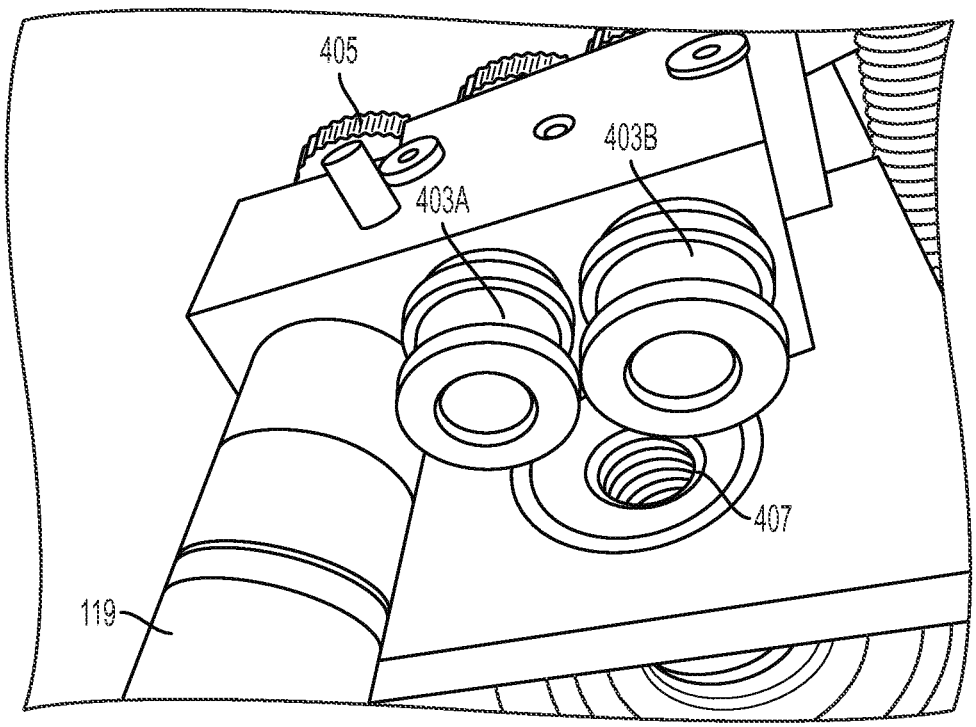
FIG. 5B is a close-up view of the insertion mechanism of the insertion motor mask of FIG. 5A.

FIG. 5A illustrates a motorized insertion mask 400 that is placed over the mouth of a patient to control advancement of the endoscope through the trachea. The mask 400 includes a patient contact rest 401 that is placed in contact with the patient's face and provides stabilized support for the insertion device 400. The motor 119 causes opposite rotation of two pinch rollers 403 that push the endoscope forward or backward. FIG. 5B shows the insertion rollers 403A and 403B in further detail. As shown in FIG. 5B, the motor 119 is coupled to both the first roller 403A and the second roller 403B by a series of gears or belts 405. As the first roller 403A moves in a clockwise fashion, the second roller 403B moves counterclockwise to push the endoscope through an opening 407 in the mask.

Figure 6A:
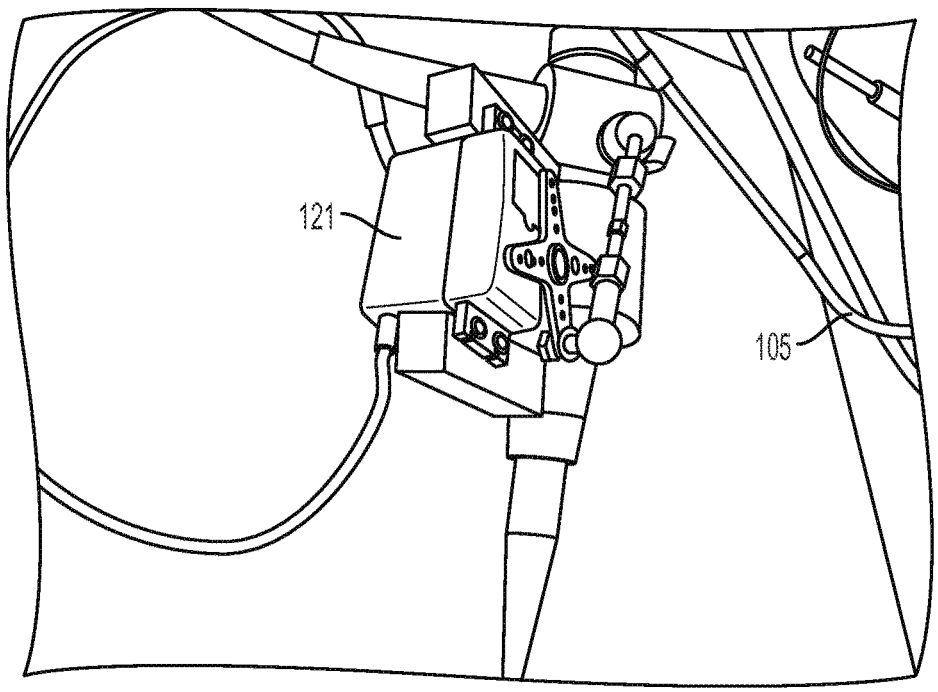
FIG. 6A is a perspective view of the lateral movement drive mechanism for the endoscope of the system of FIG. 1.
Figure 6B:
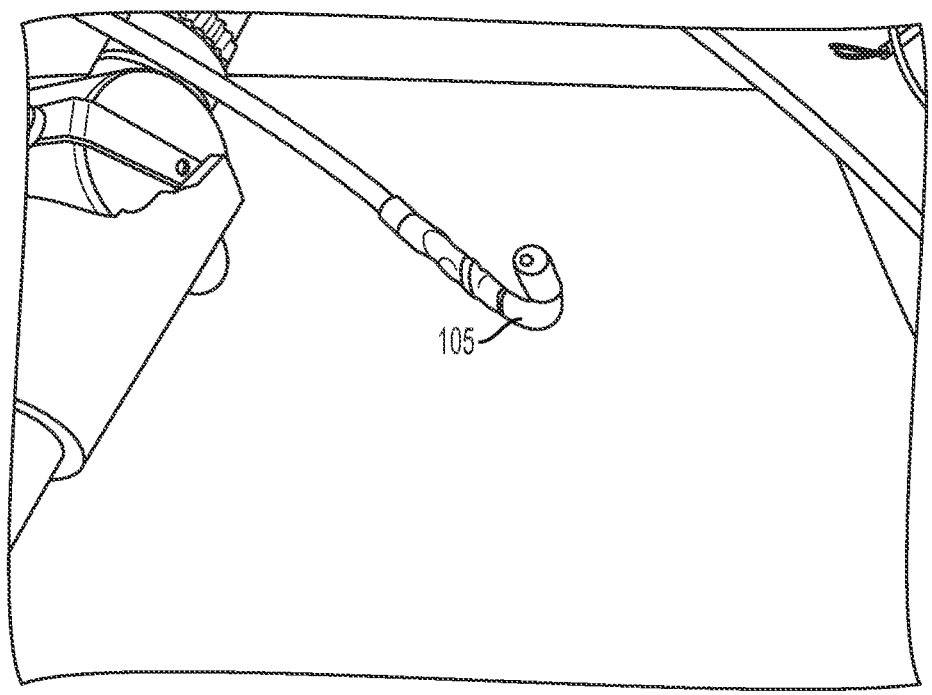
FIG. 6B is a close-up view of the controllable tip of the endoscope of the system of FIG. 1 that is driven by the drive mechanism of FIG. 6A.

FIG. 6A illustrates an example of a drive mechanism 121 that controls lateral movement of the distal tip of the endoscope 105. FIG. 6B shows the controllable tip of the endoscope 105 in further detail. The drive mechanism 121 is capable of steering the distal tip of the endoscope 105 in any radial direction (i.e., up, down, left, and right).

Figure 7:
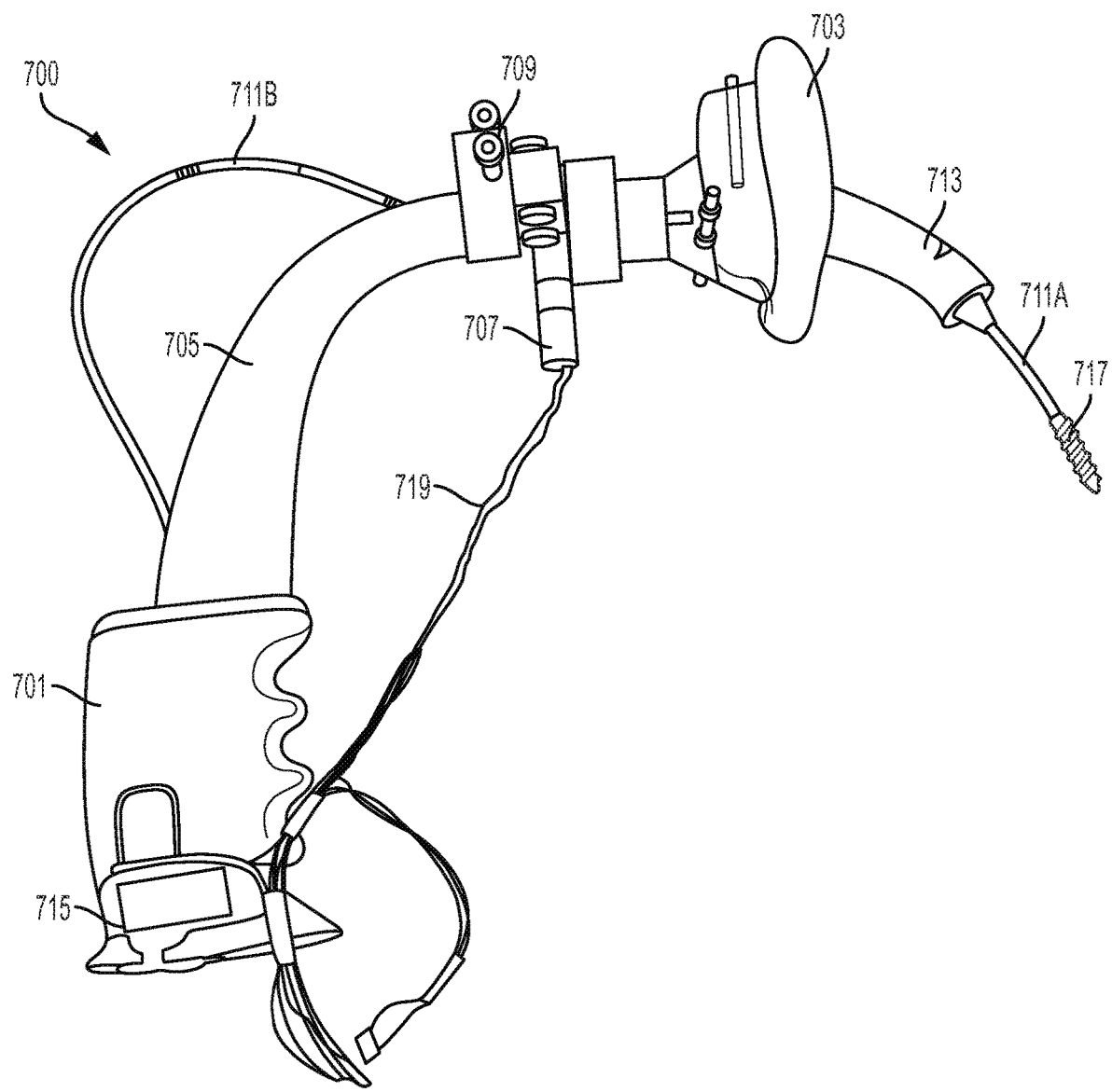
FIG. 7 is a perspective view of an example of a handheld endoscope insertion control system according to FIG. 1.

FIG. 7 illustrates another example of a device 700 for advancing an endoscope into the oral cavity of a patient. In the handheld device of FIG. 7, a handle portion 701 is coupled to a patient mask 703 by a curved body 705. The patient mask 703 is constructed of a soft plastic material and is designed to rest against the face of the patient as the endoscope is inserted orally. An electronic motor 707 is positioned near the mask 703 on the curved body 705 and drives a pair of pinch rollers 709 (as discussed above) to advance an endoscope 711A & 711B into the oral cavity of the patient. Excess length of the endoscope 711B is drawn from a proximal side of the pinch roller 709 as the endoscope 711A is extended into the oral cavity of the patient.

During use, an operator holds the device 700 by the handle portion 701 and inserts a fixed endoscope stage 713 into the mouth of the patient until the mask 703 rests against the patient's face. The operator then activates a control 715 positioned on the handle portion 701 which causes the motor 707 to advance the endoscope 711A from the fixed endoscope stage 713 and into the airway of the patient. At the same time, a rotational mechanism mounted inside the handle portion 701 rotates the endoscope 711B. Rotation of the endoscope 711B causes corresponding rotation of a soft auger 717 positioned on the distal tip of the endoscope 711B. Rotation of the soft auger 717 pulls the endoscope 711A into the airway of the patient for a combined push and pull force.

In the example of FIG. 7, the controller is housed within the handle portion 701 and coupled to the motor 707 by one or more cables 719. Although these cables 719 are shown as exposed in the example of FIG. 7, in other implementations, the cables 719 may be housed within the curved body 705 of the device 700.

Figure 8:
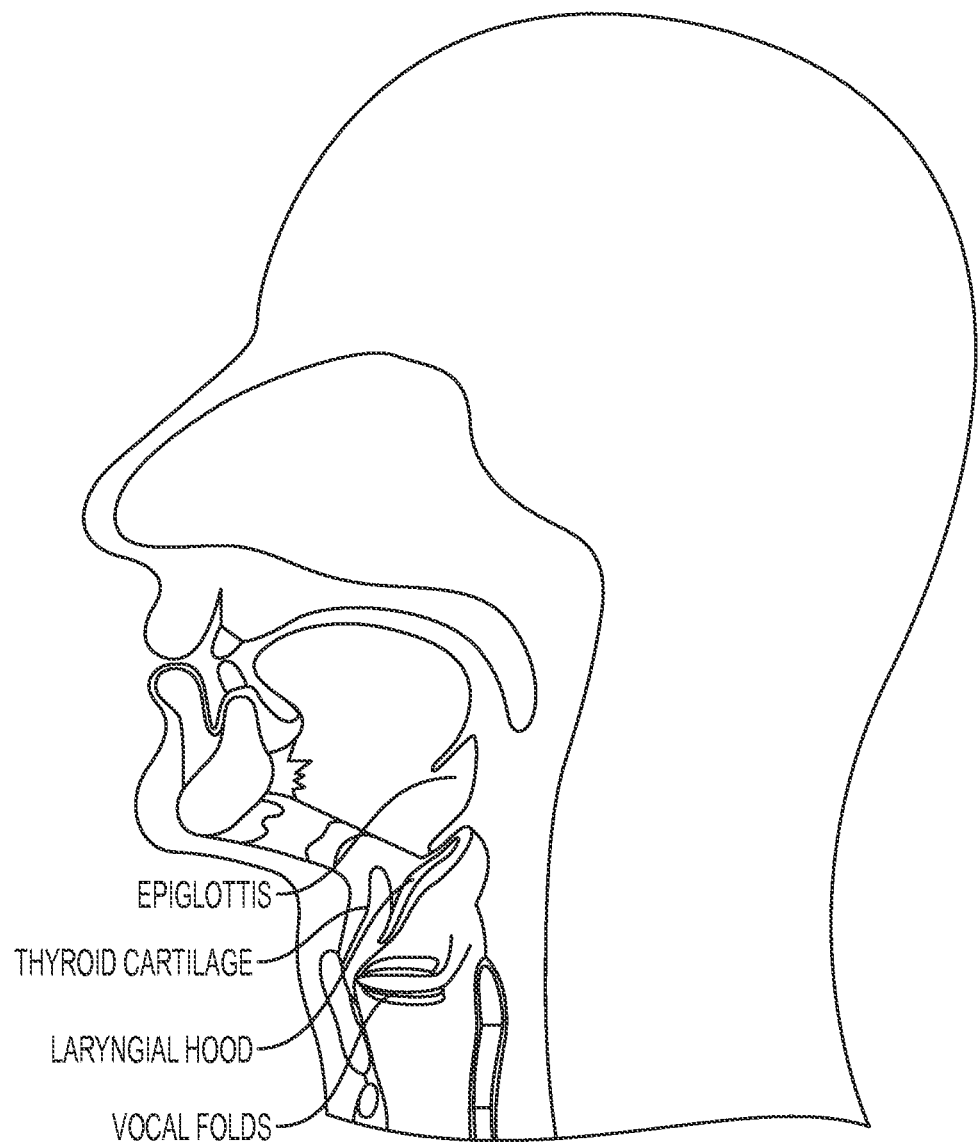
FIG. 8 is a cross-sectional view of a human airway.

FIG. 8 illustrates the anatomical pathway that the endoscope must follow during the intubation process. The tube is inserted through the mouth of the patient to the back of the oral cavity where the epiglottis is located. At the posterior of the epiglottis, the tube must be directed downward until it reaches the laryngeal hood. The tube is then moved forward to enter through the vocal folds and into the larynx.

The vibratory conductivity of these various anatomical structures varies. The epiglottis will sympathetically vibrate in response to a moving magnetic coil. When the transducer 111 vibrating at 100 Hz is placed anterolateral to the thyroid cartilage, a bridge is formed via the thyroid cartilage and epiglottis cartilage attachment. This close coupling allows for more efficient transfer of excitation frequency to the epiglottis than to the surrounding tissue.

Figure 9:
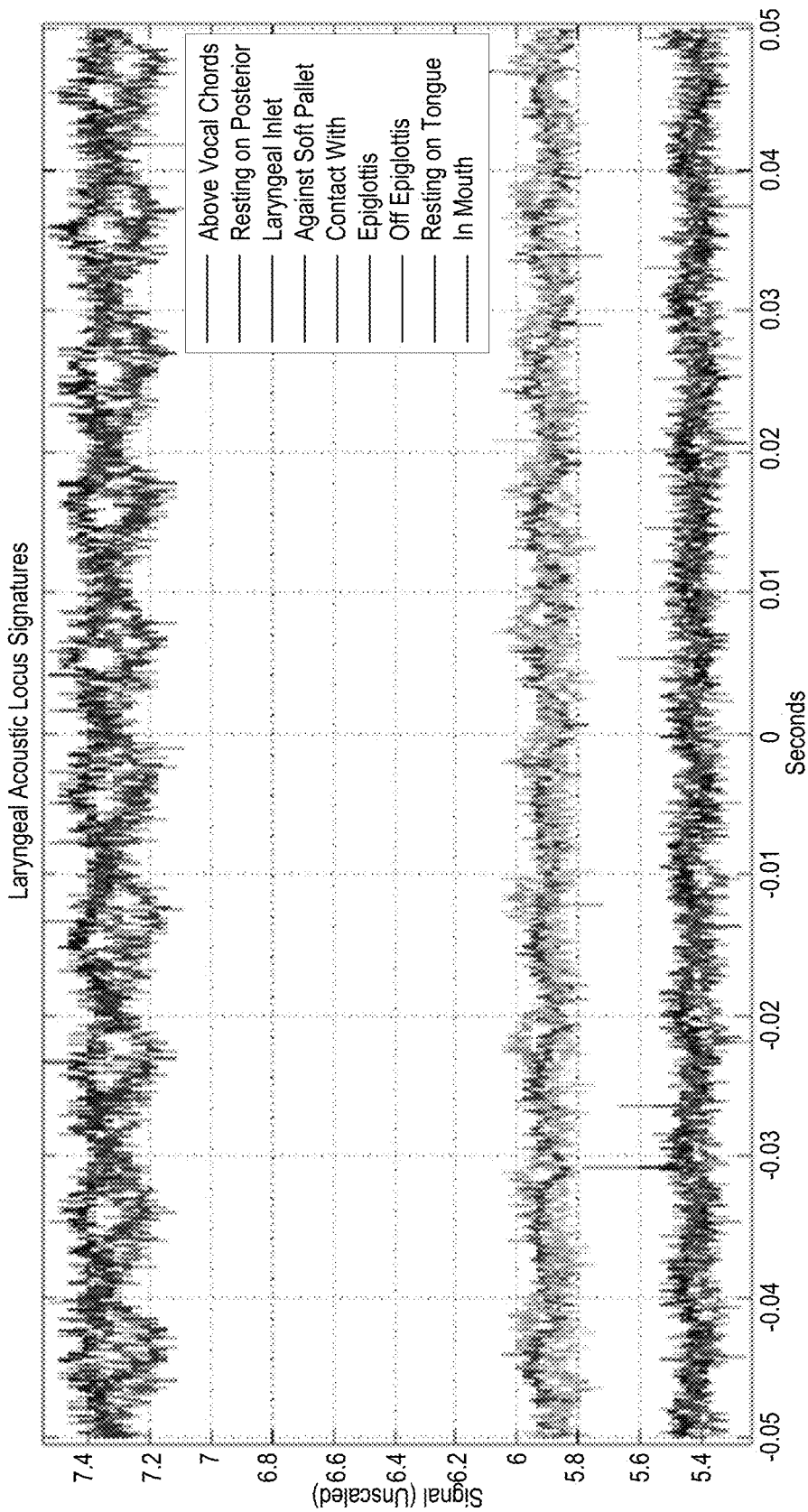
FIG. 9 is a graph of the output of an acceleration sensor in contact with various anatomic structures in response to audiovibratory stimulus generated by the loudspeaker of the system of FIG. 1.

FIG. 9 illustrates the relative output signal of the accelerometer when the distal tip of the endoscope is in contact with various different anatomical structures. Contact with the epiglottis is shown to have a marked increase in the accelerometers response relative to a distal tip located in the mouth, resting on the tongue, or positioned near, but not in contact with, the epiglottis. Due to this difference in signal conduction between soft tissue, cartilage, and the airway in close proximity to the transducer, the output signal of the accelerometer can be monitored to maintain contact with the posterior of the epiglottis and to guide the endotracheal tube towards the larynx for insertion into the vocal folds. Furthermore, if contact with the epiglottis is lost, the output signal of the accelerometer will drop.

FIG. 9 also illustrates another notable increase in the output signal of the acceleration when the distal tip of the endoscope is in contact with the anatomical structures above the vocal chords and the laryngeal inlet. This second increase can be detected and used as a second guidepost to indicate when insertion into the larynx is appropriate and insertion is completed.

Medial alignment of the endoscopic device is sensed in the magnetic domain. The same 6 DOF receiver detects the magnetic signature of the vibrating coil of the loudspeaker 111. Averaged 3-axis voltages are used to determine not only medial alignment, but also radial distance between the transducer and the distal tip of the endoscope. Quantification of the magnetic field with the endotracheal tube electronics assures location of the endotracheal tube relative to the vibrating transducer.

Figure 10:
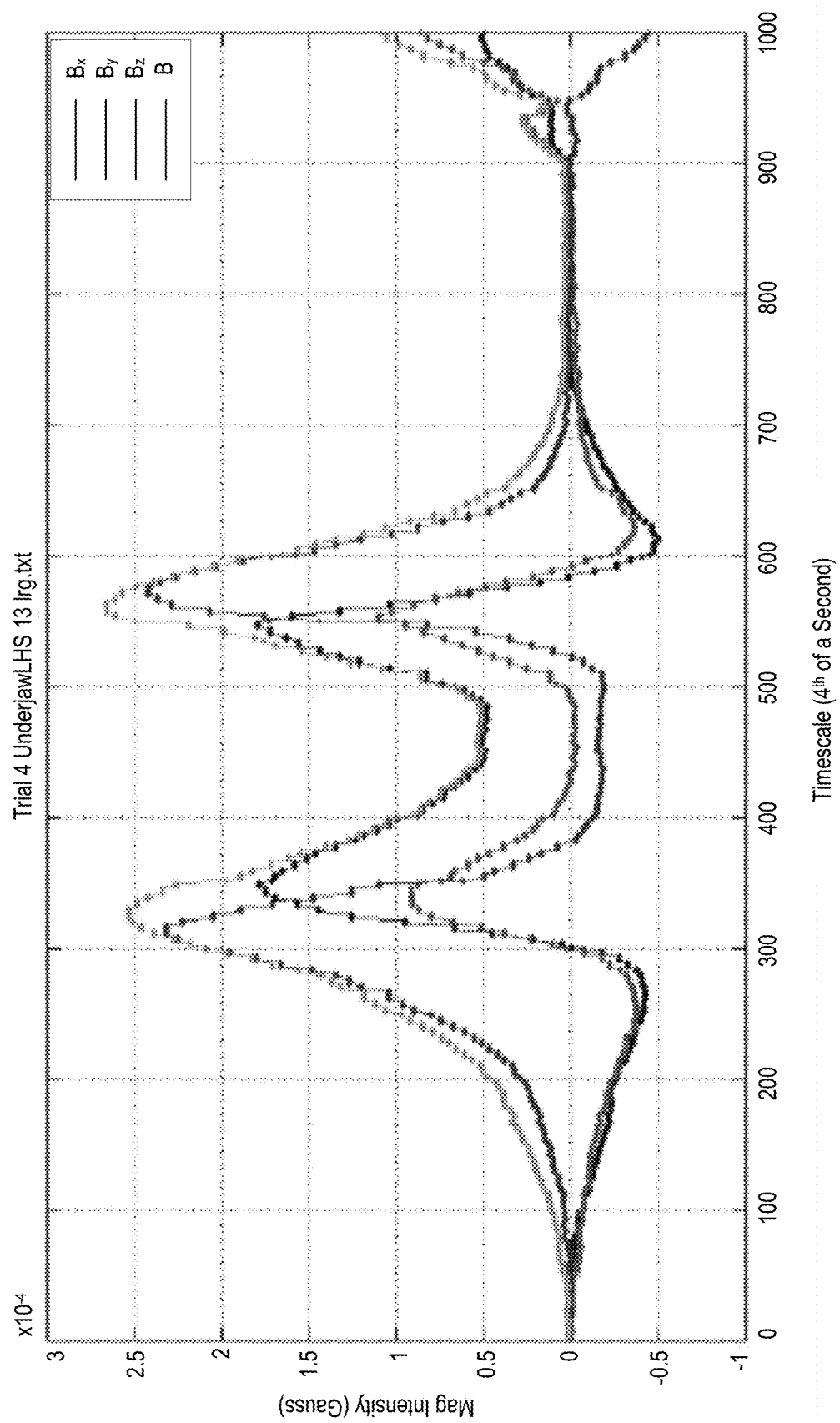
FIG. 10 is a graph of the output of the magnetic field sensor of the system of FIG. 1 at various locations in response to the magnetic field generated by the loudspeaker of the system of FIG. 1.

FIG. 10 illustrates the live stream output data from 3-axis magnetometer. The graph follows the insertion and removal of the device from the epiglottis, larynx, and vocal membranes. As illustrated by this graph, the magnetometer data can be used to track both extension and rotation of the distal tip of the endoscope throughout the entire range of motion.

Figure 11:
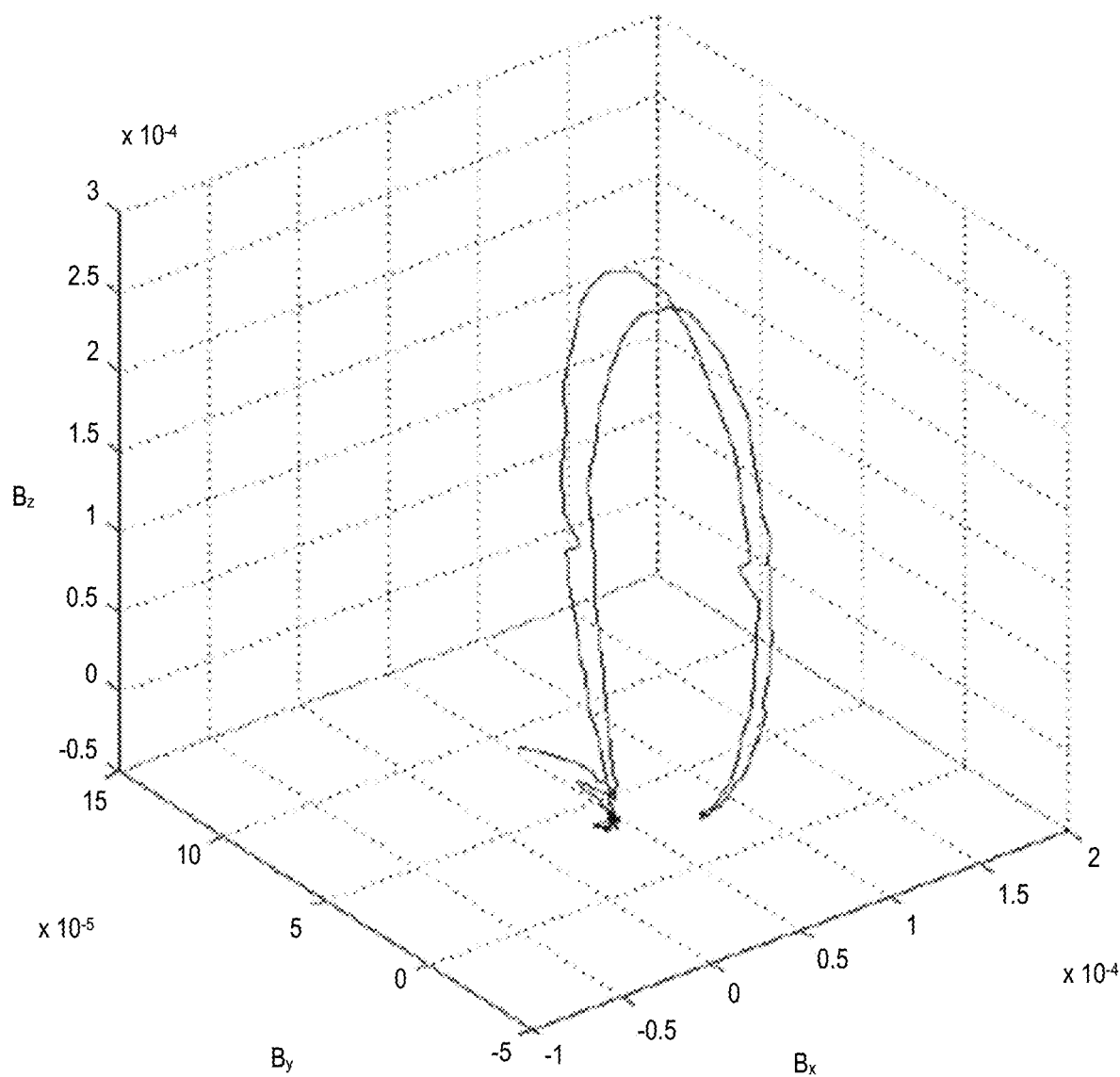
FIG. 11 is a three-dimensional graph of the magnetic field generated by the loudspeaker of the system of FIG. 1.

FIG. 11 illustrates the integration of the magnetic sensor input data in the magnetic domain. As shown in this graph, the data is both unique to each point in the trajectory and replicable. With proper calibration, the magnetometer has sensitivity to displacements as small as a millimeter and produces reliable measurements to the nearest half centimeter.

Figure 12:
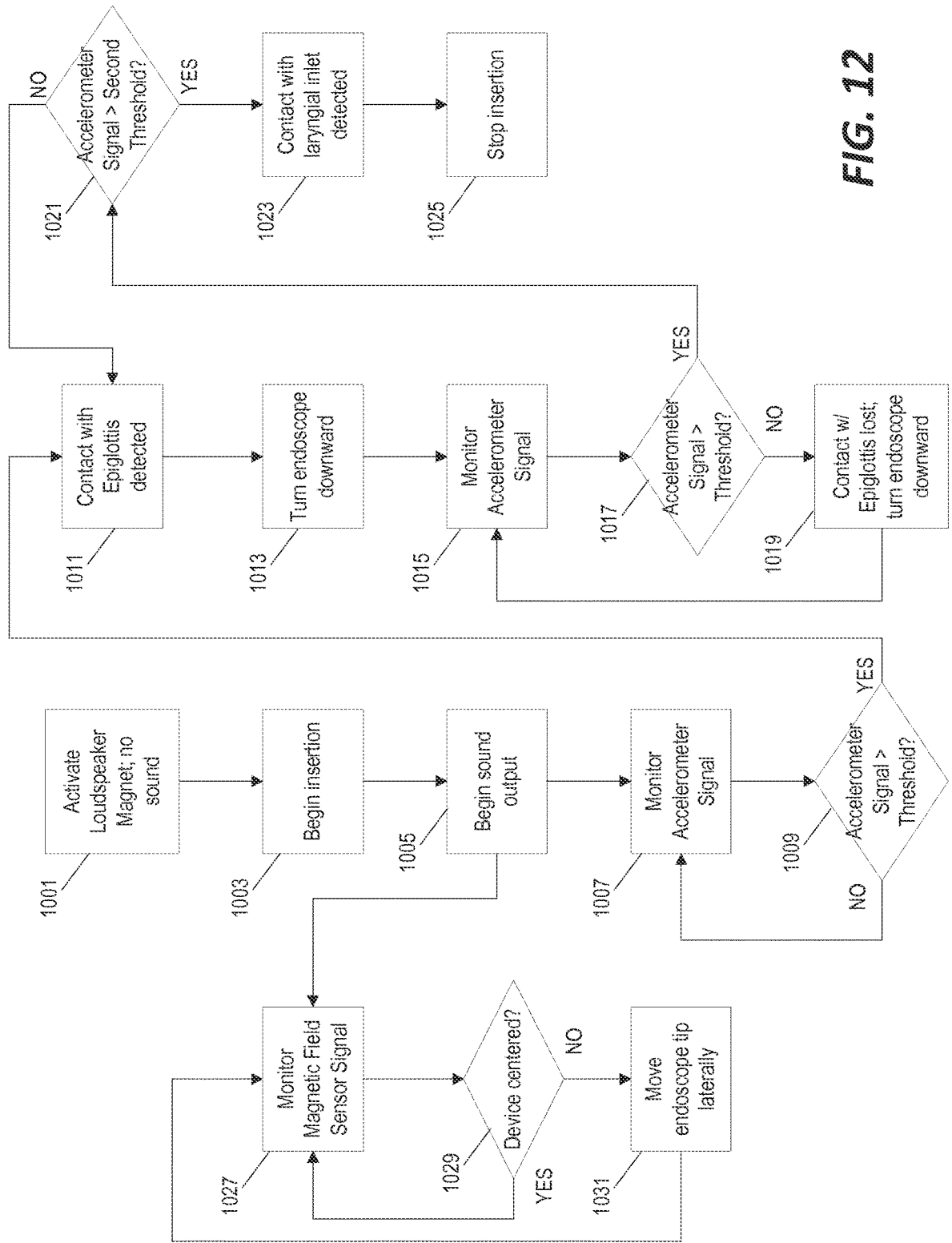
FIG. 12 is a flowchart of a method of controlled insertion of the robotic endoscope device of FIG. 1 for autonomous robotic intubation.

Based on the output of the accelerometer in response to audio vibrations and the output of the magnetometer in response to the magnetic field applied by the loudspeaker 111, the system 100 can accurately track movement of the distal tip of the endoscope as it is inserted through the trachea towards the larynx. FIG. 12 illustrates a method of autonomously controlled insertion based on these signals.

After the mask is placed on the subject, the loudspeaker magnet is activated, but no sound is initially emitted (step 1001). This allows the magnetic sensor positioned at the distal end of the endoscope to calibrate the magnetic field generated by the loudspeaker magnet. After the reference magnetic field is calibrated, the insertion motors are activated and the endoscope is advanced orally into the subject (step 1003). Sound output through the loudspeaker is then activated (step 1005).

Throughout the entire insertion process, the magnetic field generated by the loudspeaker magnet is monitored by the magnetic field sensor positioned at the distal end of the endoscope (step 1027). If a change in the observed magnetic field indicates that the distal end of the endoscope is no longer centered (step 1029), the endoscope tip is moved laterally (step 1031) so that medial alignment is properly maintained.

As the endoscope is inserted, vibrations generated by the loudspeaker are monitored by the accelerometer positioned at the distal end of the endoscope (step 1007). As discussed above, the accelerometer signal will increase notably when the tip of the endoscope makes initial contact with the epiglottis. Therefore, linear advancement of the endoscope continues until the accelerometer signal exceeds a first threshold (step 1009) indicative of contact with the epiglottis (step 1011). Once contact with the epiglottis is detected (step 1011), the tip of the endoscope is turned downward (step 1013) to follow the anatomical path towards the larynx.

The accelerometer signal is continually monitored to ensure that the tip of the endoscope remains in contact with the posterior of the epiglottis (step 1015). If the accelerometer signal drops below the threshold (step 1017), the system determines that contact with the epiglottis has been lost and the tip of the endoscope is turned further downward (step 1019) to reestablish contact between the endoscope tip and the posterior of the epiglottis.

At this point, the accelerometer signal is also compared to a second, higher threshold indicative of contact with the laryngeal inlet (step 1021). As long as the signal is greater than the first threshold and less than the second threshold, the system concludes that the tip of the endoscope is in contact with the epiglottis and insertion continues. However, once the accelerometer signal increases above the second threshold (step 1021), the system concludes that the endoscope tip is now in contact with the laryngeal inlet (step 1023). The endoscope is advanced into the larynx and the insertion motors are stopped (step 1025). A tube is then extended over the endoscope, the endoscope is removed, and intubation is complete.

As noted above, in some constructions, a gyroscopic sensor is positioned in the distal end of the endoscope. The output of the gyroscopic sensor provides a second reference to verify that intubation is on the proper medial track and also ensures that any instrument or drug delivery system is positioned at a correct orientation before administering the drug or operating the instrument. Also, because the intubation tube itself may have a natural curvature, in some constructions the gyroscopic sensor aids in placement of the intubation tube without the need for magnetic fields or a magnetometer, since the tube would tend to follow the natural bend in the throat.

Thus, the invention provides, among other things, a system and method for autonomous robotic-controlled intubation. By using feedback from accelerometers and magnetic field sensors, the system is able to accurately track movement of the device and detect contact with various specific anatomical structures to control insertion and steering of the intubation device. Various features and advantages of the invention are set forth in the following claims.

We claim:

1. A method inserting an endoscope through an anatomical cavity to a target site, the method comprising:
   positioning a speaker externally proximate to a patient;
   inserting the endoscope into the anatomical cavity;
   receiving, from at least one sensor positioned near a distal end of the endoscope, a signal indicative of vibrations induced in internal cavity tissue by the externally positioned speaker,
      wherein receiving, from the at least one sensor positioned near the distal end of the endoscope, the signal indicative of vibrations induced in the internal cavity tissue by the externally positioned speaker includes receiving, from an accelerometer positioned near the distal end of the endoscope, the signal indicative of vibrations induced in the internal cavity tissues by the externally positioned speaker;
   identifying a first anatomical structure in contact with the distal end of the endoscope based on the signal indicative of vibrations induced in the internal cavity tissue by the externally positioned speaker;
   receiving a signal from a magnetometer positioned near the distal end of the endoscope, the signal received from the magnetometer being indicative of a relative magnetic field generated by the externally positioned speaker; and
   determining whether the endoscope is centered in the anatomical cavity based on the signal from the magnetometer.

2. The method of claim 1, further comprising:
   comparing the signal indicative of vibrations induced in the internal cavity tissue by the externally positioned speaker to a contact threshold after identifying the first anatomical structure in contact with the distal end of the endoscope; and
   determining that contact between the distal end of the endoscope and the first anatomical structure has been lost when the signal indicative of vibrations induced in the internal cavity tissue by the externally positioned speaker falls below the contact threshold.

3. A method of inserting an endoscope through an anatomical cavity to a target site, the method comprising:
   positioning a speaker externally proximate to a patient;
   inserting the endoscope into the anatomical cavity;
   receiving, from at least one sensor positioned near a distal end of the endoscope, a signal indicative of vibrations induced in internal cavity tissue by the externally positioned speaker;
   identifying a first anatomical structure in contact with the distal end of the endoscope based on the signal indicative of vibrations induced in the internal cavity tissue by the externally positioned speaker;
   comparing the signal indicative of vibrations induced in the internal cavity tissue by the externally positioned speaker to a contact threshold after identifying the first anatomical structure in contact with the distal end of the endoscope;
   determining that contact between the distal end of the endoscope and the first anatomical structure has been lost when the signal indicative of vibrations induced in the internal cavity tissue by the externally positioned speaker falls below the contact threshold; and
   controllably moving the distal end of the endoscope into contact with the first anatomical structure after determining that the contact between the distal end of the endoscope and the first anatomical structure has been lost.

4. The method of claim 3, further comprising:
   advancing the endoscope further into the anatomical cavity; and
   determining that the distal end of the endoscope has moved into contact with a second anatomical structure based on a change in the signal indicative of vibrations induced in the internal cavity tissue by the externally positioned speaker.

5. The method of claim 4, further comprising identifying the second anatomical structure based on the signal indicative of vibrations induced in the internal cavity tissue by the externally positioned speaker.

6. The method of claim 5, wherein inserting the endoscope into the anatomical cavity includes inserting the endoscope into the mouth of the patient,
   wherein identifying the first anatomical structure includes identifying an epiglottis as the first anatomical structure in contact with the distal end of the endoscope, and
   wherein identifying the second anatomical structure includes identifying a laryngeal inlet as the second anatomical structure in contact with the distal end of the endoscope.

7. The method of claim 6, wherein positioning the speaker externally proximate to the patient includes positioning the speaker on the neck of the patient.

8. The method of claim 3, wherein receiving, from the at least one sensor positioned near the distal end of the endoscope, the signal indicative of vibrations induced in internal cavity tissue by the externally positioned speaker includes
   receiving, from an accelerometer positioned near the distal end of the endoscope, the signal indicative of vibrations induced in the internal cavity tissues by the externally position speaker.

9. An endoscope positioning and guidance system comprising:
   a speaker positionable externally proximate to the patient;
   an endoscope including at least one sensor positioned near a distal end of the endoscope;
   a turning motor configured to controllably turn the distal end of the endoscope; and
   a controller configured to
      receive, from the at least one sensor positioned near the distal end of the endoscope, a signal indicative of vibrations induced in internal cavity tissue by the externally positioned speaker, and identify a first anatomical structure in contact with the distal end of the endoscope based on the signal indicative of vibrations induced in the internal cavity tissue by the externally positioned speaker, wherein the controller is further configured to compare the signal indicative of vibrations induced in the internal cavity tissue by the externally positioned speaker to a contact threshold after identifying the first anatomical structure in contact with the distal end of the endoscope, determine that contact between the distal end of the endoscope and the first anatomical structure has been lost when the signal indicative of vibrations induced in the internal cavity tissue by the externally positioned speaker falls below the contact threshold, and operate the turning motor to controllably move the distal end of the endoscope into contact with the first anatomical structure after determining that the contact between the distal end of the endoscope and the first anatomical structure has been lost.

10. The endoscope positioning and guidance system of claim 9, wherein the controller is further configured to determine that the distal end of the endoscope is no longer in contact with the first anatomical structure and has moved into contact with a second anatomical structure based on a change in the signal indicative of vibrations induced in the internal cavity tissue by the externally positioned speaker.

11. The endoscope positioning and guidance system of claim 9, further comprising a motorized advancement stage configured to controllably advance the endoscope further into the anatomical cavity.

12. An endoscope positioning and guidance system comprising:

a speaker positionable externally proximate to the patient;

an endoscope including at least one sensor positioned near a distal end of the endoscope;

a magnetometer positioned near the distal end of the endoscope; and a controller configured to receive, from the at least one sensor positioned near the distal end of the endoscope, a signal indicative of vibrations induced in internal cavity tissue by the externally positioned speaker, and identify a first anatomical structure in contact with the distal end of the endoscope based on the signal indicative of the vibrations induced in the internal cavity tissue by the externally positioned speaker, and wherein the controller is further configured to receive a signal from the magnetometer indicative of a magnetic field generated by the externally positioned speaker, and determine whether the endoscope is centered in the anatomical cavity based on the signal from the magnetometer.

13. The endoscope positioning and guidance system of claim 12, further comprising a turning motor configured to controllably turn the distal end of the endoscope.

* * * * *